(12) United States Patent
Byrum

(10) Patent No.: US 7,762,999 B2
(45) Date of Patent: Jul. 27, 2010

(54) INJECTION PORT

(75) Inventor: Randal T. Byrum, Kings Mills, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1065 days.

(21) Appl. No.: 11/344,850

(22) Filed: Feb. 1, 2006

(65) Prior Publication Data
US 2007/0185462 A1   Aug. 9, 2007

(51) Int. Cl.
*A61M 37/00* (2006.01)
(52) U.S. Cl. .................................. 604/288.02
(58) Field of Classification Search ............... 604/174, 604/175, 179, 288.01–288.04
See application file for complete search history.

(56) References Cited

U.S. PATENT DOCUMENTS

| | | | |
|---|---|---|---|
| 4,685,447 A | 8/1987 | Iverson et al. | |
| 4,692,146 A | 9/1987 | Hilger | |
| 4,710,174 A * | 12/1987 | Moden et al. | 604/175 |
| 4,762,517 A | 8/1988 | McIntyre et al. | |
| 4,781,680 A | 11/1988 | Redmond et al. | |
| 4,904,241 A * | 2/1990 | Bark | 604/288.02 |
| 4,978,338 A | 12/1990 | Melsky et al. | |
| 5,006,115 A | 4/1991 | McDonald | |
| 5,013,298 A | 5/1991 | Moden et al. | |
| 5,041,098 A * | 8/1991 | Loiterman et al. | 604/175 |
| 5,045,060 A * | 9/1991 | Melsky et al. | 604/288.02 |
| 5,090,954 A | 2/1992 | Geary | |
| 5,133,753 A | 7/1992 | Bark et al. | |
| 5,185,003 A * | 2/1993 | Brethauer | 604/288.02 |
| 5,476,460 A * | 12/1995 | Montalvo | 604/891.1 |
| 5,718,682 A * | 2/1998 | Tucker | 604/288.02 |
| 5,743,873 A | 4/1998 | Cai et al. | |
| 5,792,104 A * | 8/1998 | Speckman et al. | 604/288.02 |
| 6,190,352 B1 * | 2/2001 | Haarala et al. | 604/93.01 |

(Continued)

FOREIGN PATENT DOCUMENTS

WO    WO 02/074381    9/2002

OTHER PUBLICATIONS

EPO Search Report, Application No. 07250406.1, May 14, 2007, pp. 1-7.

(Continued)

*Primary Examiner*—Kevin C Sirmons
*Assistant Examiner*—Andrew M Gilbert
(74) *Attorney, Agent, or Firm*—Frost Brown Todd LLC

(57) ABSTRACT

A port, which may be used with a gastric banding assembly, having a septum therein that is subjected to multi-directional compression forces to aid in sealing imperfections caused by multiple needle sticks. Multi-directional compression forces, including axial compression and radial compression, may be created by providing a tapered septum. Such multi-directional compression forces may also be created by providing a tapered lead-in for inserting a septum into a port body.

18 Claims, 4 Drawing Sheets

U.S. PATENT DOCUMENTS

| | | |
|---|---|---|
| 6,461,292 B1 | 10/2002 | Forsell |
| 6,470,892 B1 | 10/2002 | Forsell |
| 6,478,783 B1 | 11/2002 | Moorehead |
| 6,527,754 B1 | 3/2003 | Tallarida et al. |
| 6,962,577 B2 | 11/2005 | Tallarida et al. |
| 2003/0105385 A1 | 6/2003 | Forsell |
| 2003/0114729 A1 | 6/2003 | Forsell |
| 2004/0254536 A1 | 12/2004 | Conlon et al. |
| 2004/0254537 A1* | 12/2004 | Conlon et al. ............... 604/175 |
| 2005/0131352 A1 | 6/2005 | Conlon et al. |
| 2005/0256500 A1* | 11/2005 | Fujii ......................... 604/523 |
| 2006/0178648 A1* | 8/2006 | Barron et al. .......... 604/288.02 |

OTHER PUBLICATIONS

European Communication dated Feb. 27, 2008 for Application No. 07250406.

European Communication dated Jun. 15, 2009 for Application No. 07250406.

\* cited by examiner

INJECTION PORT

TECHNICAL FIELD

The present invention relates generally to medical implants and appliers and, more particularly, to an injection port for use with a variety of medical implants and appliers. The invention will be disclosed in connection with, but not limited to, surgically implantable injection ports and an applier therefor.

BACKGROUND

Injection ports are generally placed beneath the skin of a patient and have a variety of uses such as, for example, infusing medication, blood draws, and adjusting gastric bands. Since the early 1980s, adjustable gastric bands have provided an effective alternative to gastric bypass and other irreversible surgical weight loss treatments for the morbidly obese. A gastric band is generally wrapped around an upper portion of a patient's stomach such that a stoma is formed that restricts the passage of food from an upper portion to a lower portion of the stomach. When the gastric band is in place, and when the stoma is of the appropriate size, food held in the upper portion of the stomach provides a feeling of fullness that discourages overeating. However, initial maladjustment of the gastric band, or a change in the stomach over time, may lead to a stoma of inappropriate size that warrants adjusting the gastric band. For example, a patient may suffer vomiting attacks and discomfort if the stoma is too small to reasonably pass food. If the stoma is too large, and fails to slow food moving from the upper portion of the stomach, the gastric band may need to be tightened.

Gastric bands are generally adjusted with an inwardly directed inflatable balloon, similar to a blood pressure cuff, into which fluid, such as saline, is injected. Fluid and the like is frequently injected into the inflatable balloon with a fluid injection port that may be used to achieve a desired diameter. Because adjustable gastric bands generally remain in the patient for long periods of time, the fluid injection port is typically installed subcutaneously to avoid infection. Adjusting the amount of fluid in the adjustable gastric band is generally achieved by inserting a Huber needle through the skin into a silicon septum of the injection port. Once the needle is removed, the septum seals against the hole. A flexible conduit communicates between the injection port and the adjustable gastric band.

The silicone septum is generally partially self-healing such that multiple needle sticks may be performed before the septum becomes ineffective. This self-healing feature is generally achieved by applying an axial compressive load to the septum when it is assembled with the injection port. This axial force is generally achieved by sandwiching the septum between two adjacent pieces during assembly such that the septum will be compressively loaded throughout the duration of the procedure. This compressive load is often able to reseal imperfections in the septum caused by needle sticks.

Although the septum has the ability to self-heal after a number of needle sticks, this ability may begin to deteriorate as the septum is continually punctured due to, in part, the inability of the axial compressive load to reseal imperfections. Because injection ports are generally implantable, a gastric banding procedure or the like may have to be shortened or interrupted in order to remove and/or replace an injection port where a septum has become less effective or ineffective. Such a procedure may increase the costs to both the patient and the hospital and may pose a health risk to the patient if a surgical procedure is required to remove the injection port. Additionally, a gastric band or the like may be less effective if fluids or the like are able to diffuse or leak out as the septum loses integrity.

It would therefore be advantageous to provide a septum that has a longer useful life. It would be further advantageous to provide a septum that effectively reseals after a plurality of needle sticks and may be more easily assembled using conventional assembly mechanisms.

BRIEF SUMMARY OF THE INVENTION

Disclosed is a gastric banding assembly including a gastric band and an injection port, where the injection port is coupled to the gastric band with a delivery portion. The injection port includes a septum retainer having a base and a collar. The gastric banding assembly further includes a septum, where the septum includes a tapered surface operably configured to engage the septum retainer such that multi-directional compression forces act upon the septum when housed within the septum retainer.

Disclosed is a port that includes a port body having a septum retainer therein. The port further includes a septum, where the septum includes a tapered surface operably configured to engage the septum retainer such that multi-directional compression forces act upon the septum when housed within the septum retainer.

Disclosed is a port that includes a port body with a septum retainer housed therein, where the septum retainer includes a base and a collar. The port further includes a septum, where the septum may be retained within the base and the collar when the septum retainer is assembled, such that multi-directional compression forces act upon the septum.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
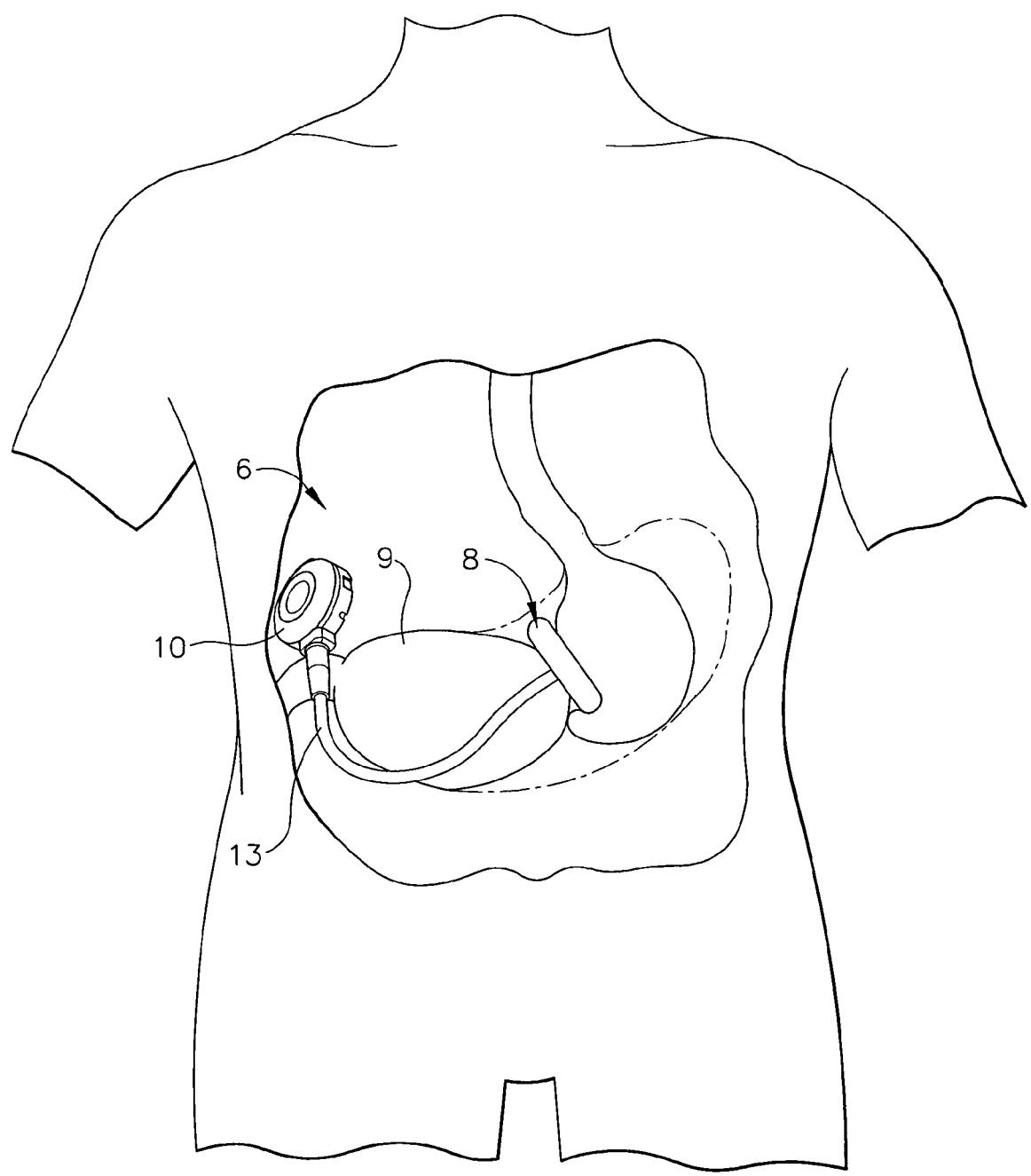
FIG. 1 is an environmental view of a gastric band placed about a stomach with an injection port attached thereto.

Reference will now be made in detail to the present preferred embodiment of the invention, an example of which is illustrated in the accompanying drawings.

DETAILED DESCRIPTION

In the following description, like reference characters designate like or corresponding parts throughout the several views. Also, in the following description, it is to be understood that terms such as front, back, inside, outside, and the like are words of convenience and are not to be construed as limiting terms. Terminology used in this patent is not meant to be limiting insofar as devices described herein, or portions thereof, may be attached or utilized in other orientations.

Referring in more detail to the drawings, an embodiment of the invention will now be described.

Referring to FIG. 1, an environmental view of one version of a gastric band assembly 6 is shown having a gastric band 8 connected to an injection port 10 by a delivery portion 13. The gastric band 8 may be placed about the patient's stomach 9 such that the delivery or removal of fluid or the like via the injection port 10 will adjust the size of the stoma created by the gastric band 8. The injection port 10 may be retained within the patient's body, such as by affixing the injection port 10 to the patient's musculature, such that access to the gastric band assembly is achieved by inserting a Huber needle or the like into the patient and into the injection port 10.

Figure 2:
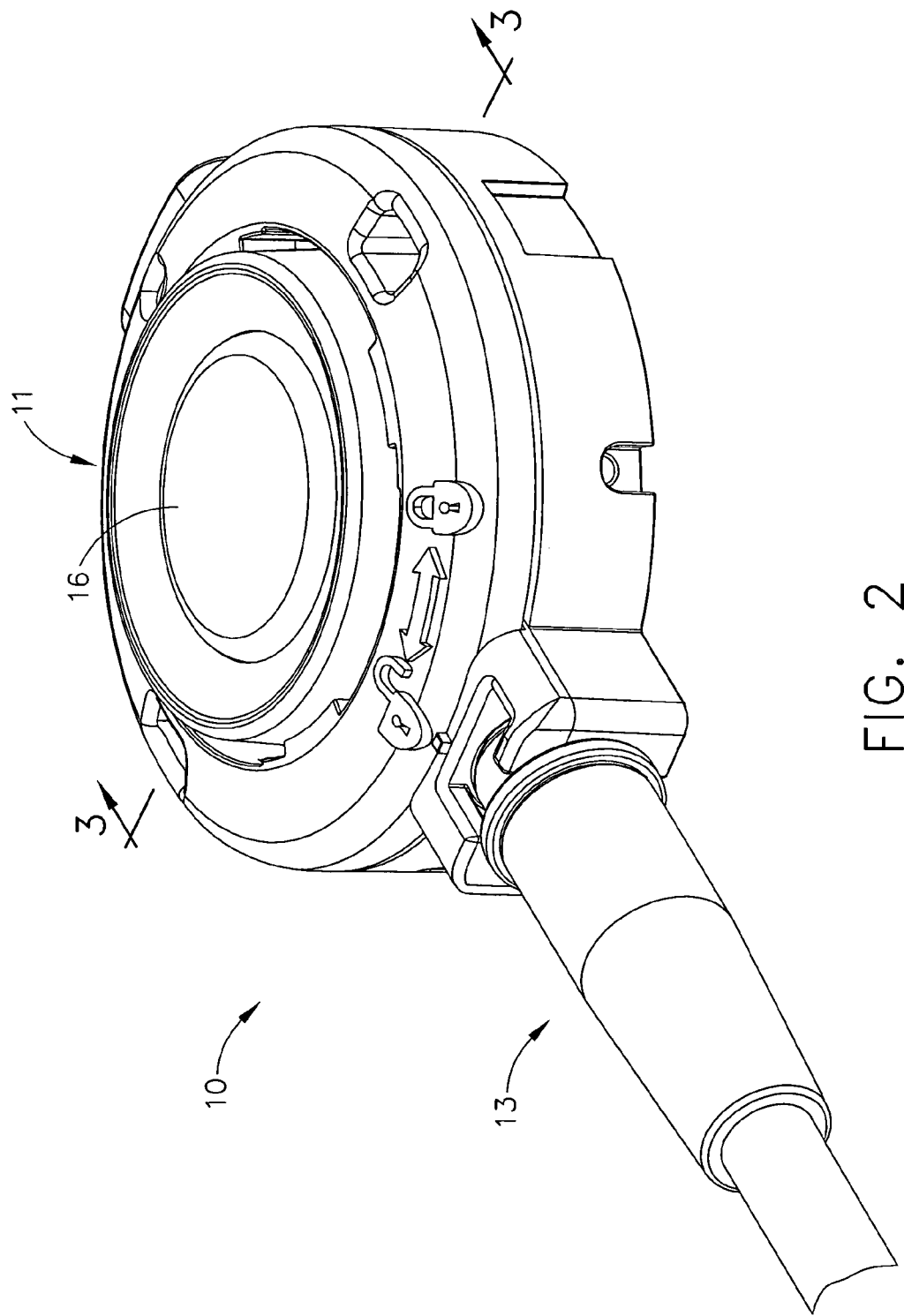
FIG. 2 is a perspective view of the injection port of FIG. 1 having a port body configured to house a septum therein.

Referring to FIG. 2, an implantable injection port 10 has a port body 11 and a delivery portion 13, where the port body 11 is configured to house a septum 16 therein. Versions of the septum 16 and port body 11 disclosed herein may be used with any suitable port or delivery means such as those, for example, disclosed in co-pending U.S. patent application Ser. No. 10/741,875, filed Dec. 19, 2003, titled "Subcutaneous Self Attaching Injection Port With Integral Moveable Retention Members" which is incorporated by reference in its entirety to the extent that it does not limit the scope of the invention. Additionally, this application incorporates by reference, to the extent that they are not limiting, the following United States patent applications, all of which were filed on Dec. 19, 2003: application Ser. No. 10/741,127 titled "Subcutaneous Injection Port For Applied Fasteners"; application Ser. No. 10/10,741,875 titled "Subcutaneous Self Attaching Injection Port With Integral Moveable Retention Members"; and application Ser. No. 10/741,868 titled "Subcutaneous Self Attaching Injection Port With Integral Fasteners". It will be appreciated that the septum 16 may be used with any implantable medical device for which it is suited, including by way of example only, pace makers, vascular access ports, injection ports, such as those used with gastric bands, and gastric pacing devices.

Figure 3:
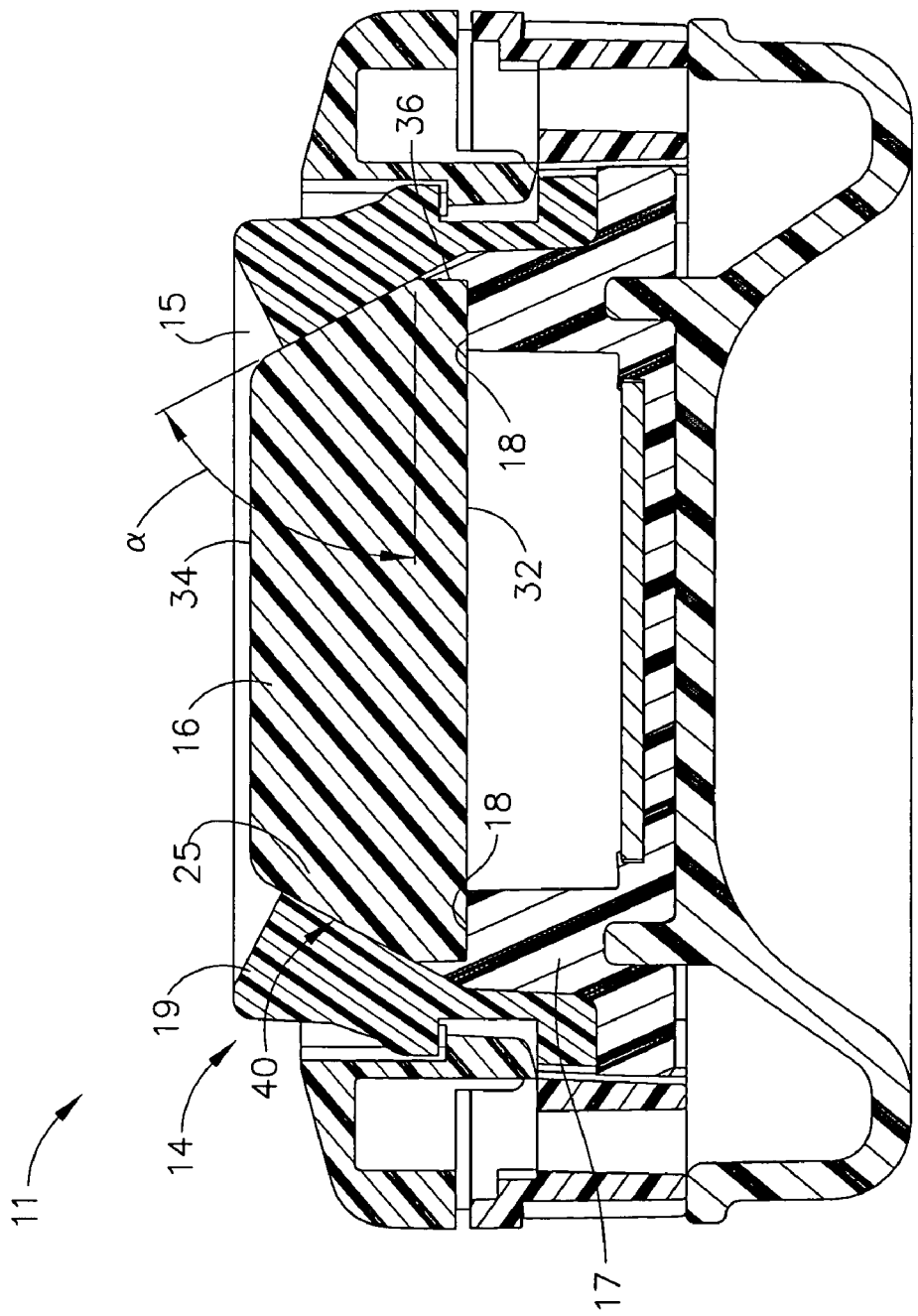
FIG. 3 is a front cross-section view, taken along line 3-3, of the injection port of FIG. 2.

Referring to FIG. 3, the port body 11 includes a septum retainer 14, configured as a substantially annular band, that includes a base 17 and a collar 19 operably configured to retain a septum 16 therein. The base 17 and collar 19 of the septum retainer 14, when coupled, may be operably configured to provide radial and axial compression forces to the septum 16. The collar 19 further includes an annular rim 15 through which the septum 16 may protrude when retained within the internal cavity 25 of the septum retainer 14.

In one version, as illustrated in FIG. 3, the septum 16 is a substantially conical disk having a bottom surface 32, a top surface 34, and a tapered surface 40. The septum 16 may taper from the bottom surface 32 to the top surface 34 where, for example, the diameter of the bottom surface 32 is greater than that of the top surface 34. In one version, by tapering the septum 16, and by configuring the collar 19 with a corresponding taper, the septum 16 may be compressed radially as the collar 19 pushes inward during assembly. This inward compression may create radial compression that beneficially reseals imperfections within the septum 16 after it is stuck with a needle. In one version, the septum 16 includes a base 36 that is not tapered, where the base may be configured to sit flush with the annular flat 18 of the base 17 for support. The septum 16 may initially be larger than the internal cavity 25 such that it must be compressed when the base 17 and the collar 19 are assembled to fit therein. Axial compression may be created by compressing the septum 16 between the annular rim 15 and the annular flat 18.

It will be appreciated that the septum 16 may be configured from any suitable biocompatible material such as, for example, silicone. The angle $\alpha$ of the taper, defined by the vectors of the bottom surface 34 and the tapered surface 40, may be from about 10° to about 80°, from about 20° to about 70°, from about 30° to about 60°, from about 55° to about 70°, at about 65°, and/or at any other suitable angle. In one version, the septum 16 may be provided with multiple angle variations such that varying levels of radial and/or axial compression act upon the septum 16. For example, the angle of the taper at the bottom surface of the septum may be 65° and the angle of the taper towards the top surface may be 70°. It is further contemplated that the angle of the taper may gradually change and/or that the angle of the taper include a series of angle changes between which the angle remains constant.

Figure 4:
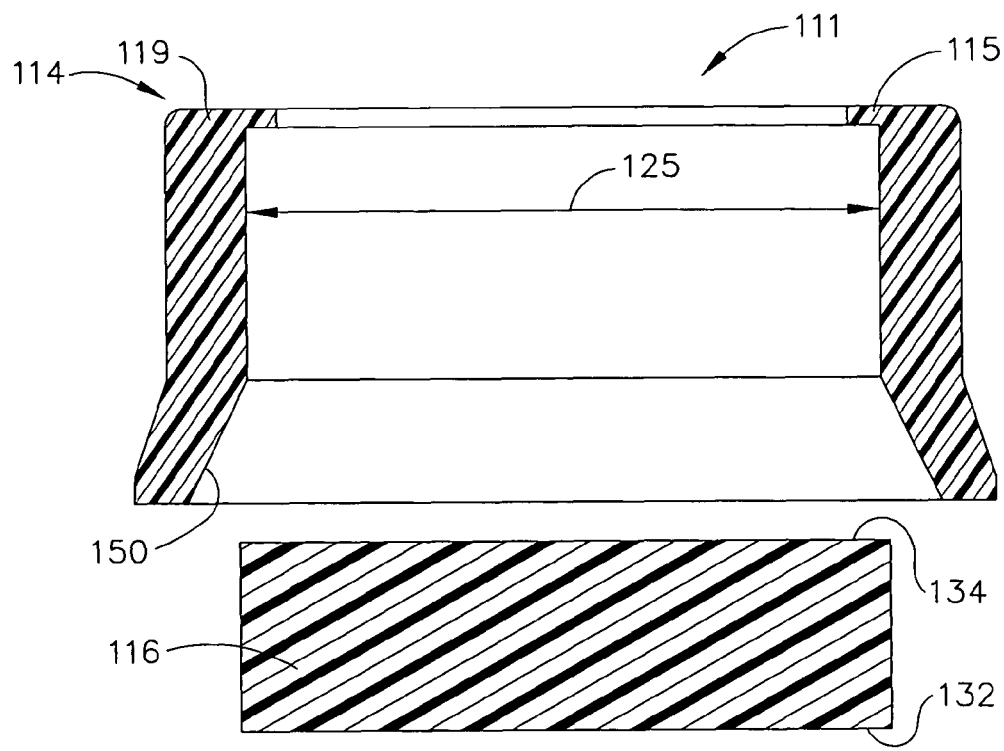
FIG. 4 is a front cross-section view, taken along line 3-3, of an alternate version of an injection port shown prior to the insertion of a septum.
Figure 5:
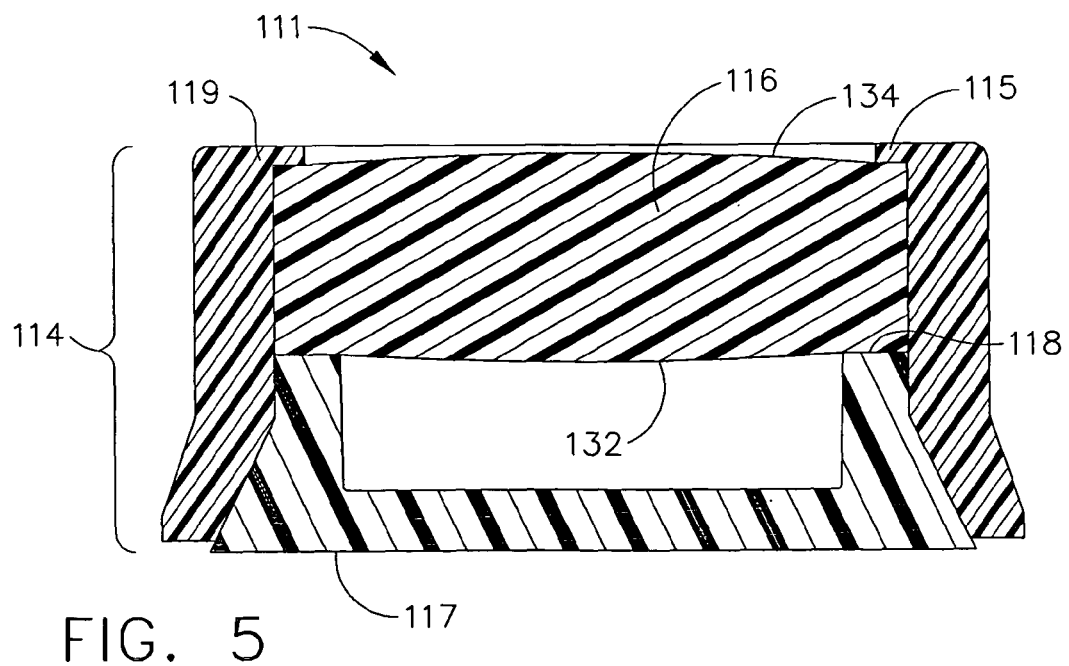
FIG. 5 is a front cross-section view, taken along line 3-3, of the injection port of FIG. 4 shown after the septum has been inserted and compressed therein.

Referring to FIGS. 4-5, an alternative version of a port body 111 is shown operably configured to apply multi-directional compression forces, such as an axial and a radial compressive force, to a septum 116. The port body 111 includes a septum retainer 114, where the septum retainer 114 is a substantially annular component that includes a base 117 and a collar 119 operably configured to retain a septum 116 therein. The base 117 and the collar 119 of the septum retainer 114, when coupled, may be operably configured to apply radial and axial compression forces against the septum 116. The collar 119 further includes an annular rim 115 through which the septum 116 may protrude.

In one version, the septum 116 is a substantially annular disk, having a bottom surface 132 and a top surface 134, that is constructed from an elastomeric material such as, for example, silicone. The septum 116 may be configured such that its diameter is greater than that of the internal cavity 125 prior to insertion. The collar 119 may be provided with an angled lead-in 150 that is operably configured to radially squeeze the septum 116 and facilitate its insertion into the internal cavity 125 during assembly. As it is inserted, the septum 116 may be compressed by the angled lead-in 150 until it fits securely within the reduced diameter of the internal cavity 125. The insertion of the elastomeric septum 116 may result in radial compression therein as the elastomeric material tries to expand against the collar 119. The radial compression of the septum 116 may facilitate resealing after one or a plurality of needle sticks.

In addition to radial compression, axial compression may be applied by coupling the base 117 with the collar 119 of the septum retainer 114. For example, the septum 116 may be axially compressed between an annular flat 118 on the base 117 and the annular rim 115 of the collar 119 during assembly. The septum 116 may be configured such that, when the base 117 and the collar 119 are coupled, the elastomeric material of the septum 116 is compressed and held, thereby creating axial compression forces therein. For example, the initial height of the septum 116 may be greater than the distance between the base 117 and collar 119 when coupled. In the illustrated version, both axial and radial compression forces may be created simultaneously to improve the resealability of the septum 116. Providing multiple compression forces may reseal those defects or the like that would remain unsealed should only a unidirectional force be provided.

It will be appreciated that the septum 116 may be configured from any suitable biocompatible and/or elastomeric material such as, for example, silicone. It will also be appreciated that the septum 116 may also include a tapered surface. The collar 119 may include any suitable angled lead-in 150 having an angle suitable for facilitating the insertion of the septum 115 into the septum retainer 114. It is further contemplated that, for example, the septum 116 may be pre-compressed prior to insertion where, upon insertion into the collar 119, the pre-compression on the septum 116 could be released such that it presses against the sides of the septum retainer 114.

Providing compressive force in multiple directions simultaneously, such as in a radial and axial direction, may increase the number of times a septum may be stuck with a needle or the like before becoming less effective or ineffective. Increasing the longevity of the septum may increase the life of the injection port and/or the accompanying medical device. Increasing the longevity of the injection port may increase the efficiency, safety, and/or accuracy of procedures and instruments with which the injection port or the like is used.

It will be appreciated that any suitable multi-directional forces may be provided by any suitable means to facilitate improved self-healing of the septum after a needle puncture. For example, multi-directional compression forces may be achieved by coupling the septum and the septum retainer with a simple arbor press adapted to apply axial pressure. The multi-directional compression forces may be achieved by the axial force of the arbor press effecting radial compression forces as the septum and the septum retainer are engaged. Multi-directional forces, such as axial compression forces and radial compression forces, may be achieved simultaneously or in succession. For example, in one version, a septum and a septum retainer may be axially compressed when assembled with an acorn press or the like. Radial compression may then be achieved by providing the septum retainer with an annular band around the circumference thereof that, when adjusted, applies radial pressure to the septum in addition to the compressive axial force created by the acorn press.

It will be appreciated that the septum and/or septum retainer may be configured to apply any suitable level of compressive force, unidirectionally or multi-directionally. For example, adjusting the angle of the septum taper, providing a taper with varying angles, adjusting the angle of the septum retainer taper, adjusting the shape or size of the annular flat, altering the size of the septum, altering the shape of the angled lead-in, and/or adding a radial compression band (not shown), may create or modify the multi-directional forces. The septum retainer, the port body, and/or any other components may be made of any suitable material having sufficient stiffness and strength such as, for example, polyetheretherketon (known as PEEK).

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention may be alternatively described as a means for performing that element's function.

For example, it will become readily apparent to those skilled in the art, given the benefit of the present disclosure, that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. Patent Application 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. Patent Application Publ. No. 2003/0114729, which is hereby incorporated herein by reference. Further, a hydraulically inflatable therapeutic member may comprise an exteriorly adjustable bladder that actuates by expanding in length and/or outer diameter, such as a penile implant.

What is claimed is:

1. A port comprising:
   (a) a port body having a septum retainer therein, wherein the septum retainer comprises a collar and a base, the collar having an inner surface extending about a circumference of the collar, wherein the inner surface of the collar is configured to have a substantially straight taper at a predetermined angle, wherein the base is configured to have a substantially straight taper that complements the substantially straight taper of the inner surface of the collar, wherein the base is further configured to couple with the inner surface of the collar; and
   (b) a septum, wherein the septum has a lower surface, a side surface, and a tapered surface, wherein the side surface is substantially perpendicular to the lower surface, wherein the base of the port body engages the lower surface of the septum and the side surface of the septum, wherein the inner surface of the collar of the port body engages the tapered surface of the septum, wherein the septum is retained and compressed by the coupling of the collar and the base, and wherein said tapered surface of the septum is operably configured to engage said septum retainer such that multi-directional compression forces act upon said septum when housed within said septum retainer.

2. The port of claim 1, wherein said septum is configured from an elastomeric material.

3. The port of claim 2, wherein said septum is configured from silicone.

4. The port of claim 1, wherein said multi-directional compression forces are axial compression forces and radial compression forces applied to said septum such that imperfections caused by needle sticks are substantially self-healed.

5. The port of claim 1, wherein said multi-directional compression forces are created by coupling said septum and said septum retainer with an acorn press.

6. A port comprising:
   (a) a port body;
   (b) a septum retainer housed within said port body, wherein said septum retainer comprises a base and a collar, the collar having an upper annular rim, a lower annular rim, and an obliquely angled surface sloping from the upper annular rim to the lower annular rim, wherein the diameter of the upper annular rim is greater than the diameter of the lower annular rim, wherein the lower annular rim defines a plane, wherein the base includes an upwardly presented surface and an inwardly presented surface; and
   (c) a septum, wherein said septum comprises a lower surface, a side surface, and a substantially straight tapered surface, wherein the lower surface of the septum is disposed upon the upwardly presented surface of the base, wherein the side surface of the septum engages the inwardly presented surface of the base, wherein the side surface is substantially perpendicular to the lower surface of the septum, wherein at least a portion of the septum protrudes above the plane defined by the lower annular rim, wherein the collar engages the substantially straight tapered surface of the septum such that the septum is retained within said base and said collar when said septum retainer is assembled such that multi-directional compression forces act upon said septum.

7. The port of claim 6, wherein said septum is configured from an elastomeric material.

8. The port of claim 7, wherein said septum is configured from silicone.

9. The port of claim 6, wherein said septum has a initial diameter greater than that of an internal cavity within said septum retainer, where compressing said septum into said internal cavity creates radial compression forces that act upon said septum.

10. The port of claim 9, wherein said septum has a initial height greater than that of the internal cavity between said base and the lower annular rim of said collar, where coupling said base and said collar compresses said septum such that axial compression forces are created that act upon said septum.

11. The port of claim 9, wherein the obliquely angled surface provides a lead-in operably configured to aid in the insertion and compression of said septum into said internal cavity.

12. The port of claim 11, wherein said septum retainer and said septum are coupled with an acorn press.

13. The port of claim 9, wherein said septum retainer and said septum are coupled with an acorn press.

14. The port of claim 6, wherein said multi-directional compression forces are axial compression forces and radial compression forces.

15. A gastric banding assembly comprising:
    (a) a gastric band;
    (b) an injection port, where the injection port is coupled to said gastric band with a delivery portion configured therebetween;
    (c) a septum retainer housed within said injection port, where said septum retainer comprises a base and a collar, wherein the collar has an inner surface extending about a circumference of the collar, wherein the inner surface of the collar is configured to have a substantially straight taper, wherein the base is configured to have a substantially straight taper that complements the substantially straight taper of the inner surface of the collar, wherein the base is configured to couple with the inner surface of the collar; and
    (d) a septum, wherein the septum has a lower surface, a side surface, and a tapered surface, wherein the side surface is substantially perpendicular to the lower surface, wherein the base is configured to engage both the lower surface of the septum and the side surface of the septum, wherein the inner surface of the collar engages the tapered surface of the septum, wherein the septum is retained and compressed by the coupling of the collar and the base such that multi-directional compression forces act upon said septum when housed within said septum retainer.

16. The gastric banding assembly of claim 15, wherein said multi-directional compression forces include axial compression forces and radial compression forces.

17. The gastric banding assembly of claim 16, wherein said septum is configured from silicone.

18. The gastric banding assembly of claim 17, wherein said substantially straight tapered surface of the collar includes at least two different angles.

* * * * *